United States Patent
Cone et al.

(10) Patent No.: US 12,144,569 B2
(45) Date of Patent: *Nov. 19, 2024

(54) ROBOTIC SURGICAL PEDAL WITH INTEGRATED FOOT SENSOR

(71) Applicant: Verb Surgical Inc., Santa Clara, CA (US)

(72) Inventors: Taylor Cone, Belmont, CA (US); Joan Savall, Palo Alto, CA (US)

(73) Assignee: Verb Surgical Inc., Santa Clara, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/470,365

(22) Filed: Sep. 19, 2023

(65) Prior Publication Data
US 2024/0058078 A1    Feb. 22, 2024

Related U.S. Application Data

(63) Continuation of application No. 18/079,696, filed on Dec. 12, 2022, now Pat. No. 11,786,320, which is a
(Continued)

(51) Int. Cl.
*A61B 34/00* (2016.01)
*A61B 17/00* (2006.01)
(Continued)

(52) U.S. Cl.
CPC .............. *A61B 34/25* (2016.02); *A61B 34/35* (2016.02); *A61B 34/76* (2016.02);
(Continued)

(58) Field of Classification Search
CPC ......... A61B 34/25; A61B 34/35; A61B 34/76; A61B 2017/00199; A61B 2017/00212;
(Continued)

(56) References Cited

U.S. PATENT DOCUMENTS

| 4,837,857 A | 6/1989 | Scheller et al. |
| 4,965,417 A | 10/1990 | Massie |

(Continued)

FOREIGN PATENT DOCUMENTS

| CN | 107874834 A | 4/2018 |
| DE | 102016105554 A1 | 9/2017 |

(Continued)

OTHER PUBLICATIONS

International Preliminary Report on Patenlability for International Application No. PCT/US2018/043554 mailed Jan. 28, 2021, 12 pages.

(Continued)

*Primary Examiner* — David P Porta
*Assistant Examiner* — Gisselle M Gutierrez
(74) *Attorney, Agent, or Firm* — Aikin & Gallant, LLP (57) ABSTRACT

A foot pedal assembly for controlling a robotic surgical system. The foot pedal assembly including a foot pedal base, a foot pedal and a sensor. The foot pedal moves relative to the foot pedal base and has a contact surface extending from a distal end to a proximal end of the foot pedal. The contact surface is to come into contact with a foot of a user during use of the foot pedal assembly for controlling the robotic surgical system and the distal end is farther away from a heel of the foot than the proximal end during use of the assembly for controlling the robotic surgical system. The sensor is coupled to the contact surface of the foot pedal at a position closer to the proximal end than the distal end, and the sensor is operable to sense a target object positioned a distance over the contact surface.

20 Claims, 9 Drawing Sheets

Related U.S. Application Data continuation of application No. 17/115,587, filed on Dec. 8, 2020, now Pat. No. 11,547,500, which is a continuation of application No. 16/038,128, filed on Jul. 17, 2018, now Pat. No. 10,888,383.

(51) Int. Cl.
*A61B 34/35* (2016.01)
*G05G 1/38* (2008.04)

(52) U.S. Cl.
CPC .............. *A61B 2017/00199* (2013.01); *A61B 2017/00212* (2013.01); *A61B 2017/00221* (2013.01); *A61B 2017/00973* (2013.01); *G05G 1/38* (2013.01)

(58) Field of Classification Search
CPC ........... A61B 2017/00221; A61B 2017/00973; A61B 2090/061; A61B 2090/065; A61B 2090/0807; A61B 34/74; A61B 34/30; G05G 1/38; G05G 1/305
See application file for complete search history.

(56) References Cited

U.S. PATENT DOCUMENTS

| | | | |
|---|---|---|---|
| 5,204,942 | A | 4/1993 | Otera et al. |
| 5,422,521 | A | 6/1995 | Neer et al. |
| 5,553,609 | A | 9/1996 | Chen et al. |
| 5,583,407 | A | 12/1996 | Yamaguchi |
| 5,635,777 | A | 6/1997 | Telymonde et al. |
| 5,704,791 | A | 1/1998 | Gillio |
| 5,787,760 | A | 8/1998 | Thorlakson |
| 5,855,553 | A | 1/1999 | Tajima et al. |
| 5,876,325 | A | 3/1999 | Mizuno et al. |
| 5,877,760 | A | 3/1999 | Onda et al. |
| 5,883,615 | A | 3/1999 | Fago et al. |
| 5,889,510 | A | 3/1999 | Klarlund |
| 5,931,832 | A | 8/1999 | Jensen |
| 6,179,829 | B1 | 1/2001 | Bisch et al. |
| 6,600,477 | B1 | 7/2003 | Howell |
| 6,646,541 | B1 | 11/2003 | Wang et al. |
| 6,659,939 | B2 | 12/2003 | Moll et al. |
| 6,852,107 | B2 | 2/2005 | Wang et al. |
| 6,892,112 | B2 | 5/2005 | Wang et al. |
| 6,951,535 | B2 | 10/2005 | Ghodoussi et al. |
| 7,245,202 | B2 | 7/2007 | Levin |
| 7,865,266 | B2 | 1/2011 | Moll et al. |
| 7,877,171 | B2 | 1/2011 | Gassner |
| 7,977,171 | B2 | 7/2011 | Yang et al. |
| 8,340,863 | B2 | 12/2012 | Karatsinides |
| 8,527,094 | B2 | 9/2013 | Kumar et al. |
| 8,914,150 | B2 | 12/2014 | Moll et al. |
| 9,039,681 | B2 | 5/2015 | Wang et al. |
| 9,119,654 | B2 | 9/2015 | Ramans et al. |
| 9,301,811 | B2 | 4/2016 | Goldberg et al. |
| 9,333,042 | B2 | 5/2016 | Diolaiti et al. |
| 9,375,288 | B2 | 6/2016 | Robinson et al. |
| 9,439,806 | B2 | 9/2016 | Eastman et al. |
| 9,666,101 | B2 | 5/2017 | Kumar et al. |
| 10,368,955 | B2 | 8/2019 | Cone et al. |
| 10,503,199 | B1 | 12/2019 | Cone et al. |
| 10,888,383 | B2 | 1/2021 | Cone et al. |
| 11,191,528 | B2 | 12/2021 | Bucina et al. |
| 11,266,385 | B1 | 3/2022 | Tseng et al. |
| 2002/0029095 | A1 | 3/2002 | Kosaka et al. |
| 2002/0107573 | A1 | 8/2002 | Steinberg |
| 2003/0013949 | A1 | 1/2003 | Moll et al. |
| 2003/0047434 | A1 | 3/2003 | Hanson et al. |
| 2003/0050733 | A1 | 3/2003 | Wang et al. |
| 2003/0060927 | A1 | 3/2003 | Gerbi et al. |
| 2006/0014611 | A1 | 1/2006 | Kitamura et al. |
| 2006/0166681 | A1 | 7/2006 | Lohbihler |
| 2006/0178559 | A1 | 8/2006 | Kumar et al. |
| 2006/0219049 | A1 | 10/2006 | Horvath et al. |
| 2007/0093868 | A1 | 4/2007 | Fugo |
| 2009/0036902 | A1 | 2/2009 | Dimaio et al. |
| 2009/0253109 | A1 | 10/2009 | Anvari et al. |
| 2010/0198200 | A1 | 8/2010 | Horvath |
| 2010/0225209 | A1 | 9/2010 | Goldberg et al. |
| 2010/0228264 | A1 | 9/2010 | Robinson et al. |
| 2011/0098721 | A1 | 4/2011 | Tran et al. |
| 2012/0029694 | A1 | 2/2012 | Mueller |
| 2012/0283745 | A1 | 11/2012 | Goldberg et al. |
| 2013/0023899 | A1 | 1/2013 | Green |
| 2013/0245834 | A1 | 9/2013 | Laxhuber et al. |
| 2013/0331859 | A1 | 12/2013 | Kumar et al. |
| 2014/0195048 | A1 | 7/2014 | Moll et al. |
| 2014/0328469 | A1 | 11/2014 | Lee et al. |
| 2014/0364864 | A1 | 12/2014 | Lynn et al. |
| 2014/0378986 | A1 | 12/2014 | Eastman et al. |
| 2015/0003898 | A1 | 1/2015 | Shiozaki |
| 2015/0029047 | A1 | 1/2015 | Levasseur et al. |
| 2015/0038981 | A1 | 2/2015 | Kilroy et al. |
| 2015/0051607 | A1 | 2/2015 | Hajishah et al. |
| 2015/0150546 | A1 | 6/2015 | Goldschmidt |
| 2015/0202014 | A1 | 7/2015 | Kim et al. |
| 2015/0323953 | A1 | 11/2015 | Klestil |
| 2016/0045365 | A1 | 2/2016 | Foster et al. |
| 2017/0007218 | A1 | 1/2017 | Lai |
| 2017/0129502 | A1 | 5/2017 | Stoffels et al. |
| 2018/0083621 | A1 | 3/2018 | Ekvall et al. |
| 2018/0099608 | A1 | 4/2018 | Salter et al. |
| 2018/0132948 | A1 | 5/2018 | Mercado |
| 2018/0250086 | A1 | 9/2018 | Grubbs |
| 2018/0280099 | A1 | 10/2018 | Cone et al. |
| 2018/0338806 | A1 | 11/2018 | Grubbs |
| 2019/0220052 | A1 | 7/2019 | Kihara et al. |
| 2019/0239971 | A1 | 8/2019 | Lim |
| 2019/0314005 | A1 | 10/2019 | Ishihara et al. |
| 2019/0388157 | A1 | 12/2019 | Shameli et al. |
| 2020/0022761 | A1 | 1/2020 | Cone et al. |
| 2021/0213942 | A1 | 7/2021 | Kayano |
| 2021/0213974 | A1 | 7/2021 | Shimbo et al. |
| 2022/0054187 | A1 | 2/2022 | Mohr et al. |
| 2022/0063404 | A1 | 3/2022 | Takabatake et al. |

FOREIGN PATENT DOCUMENTS

| | | |
|---|---|---|
| EP | 0587948 A1 | 3/1994 |
| EP | 1095642 A1 | 5/2001 |
| EP | 3085318 A1 | 10/2016 |
| WO | 2011/116332 A2 | 9/2011 |
| WO | 2014/189969 A1 | 11/2014 |
| WO | 2014/205166 A1 | 12/2014 |

OTHER PUBLICATIONS

International Search Report and Written Opinion of the PCT Patent Office dated Jun. 12, 2019 for related PCT Patent Application No. PCT/US2018/043554.

International Search Report and Written Opinion of the PCT Patent Office dated May 14, 2019 for related PCT Patent Application No. PCT/US2018/043557.

Invitation to Pay Additional Fees of the PCT Patent Office dated Apr. 11, 2019 for related PCT Patent Application No. PCT/US2018/043554.

Invitation to Pay Additional Fees of the PCT Patent Office dated Mar. 18, 2019 for related PCT Patent Application No. PCT/US2018/043557.

ROBOTIC SURGICAL PEDAL WITH INTEGRATED FOOT SENSOR

CROSS-REFERENCE TO RELATED APPLICATIONS

This application is a continuation of pending U.S. patent application Ser. No. 18/079,696, filed Dec. 12, 2022, which is a continuation of U.S. patent application Ser. No. 17/115,587, filed Dec. 8, 2020, now U.S. Pat. No. 11,547,500, issued Jan. 10, 2023, which is a continuation of U.S. patent application Ser. No. 16/038,128, filed on Jul. 17, 2018, now U.S. Pat. No. 10,888,383, issued Jan. 12, 2021, which are hereby incorporated by this reference in their entirety.

FIELD

An embodiment of the invention relates to a robotic surgical pedal with integrated foot sensor for sensing a presence and/or location of a user's foot. Other embodiments are also described.

BACKGROUND

In a robotic surgical system, a robotic arm has a surgical tool attached to its distal end that is remotely operated by a surgeon. Applications include endoscopic surgery, which involves looking into a patient's body and performing surgery inside, for example the abdominal cavity, using endoscopes and other surgical tools that are attached to the ends of several robotic arms. The system gives the surgeon a close-up view of the surgery site, and also lets the surgeon operate the tool that is attached to the arm, all in real-time. The tool may be a gripper with jaws, a cutter, a video camera, or an energy emitter such as a laser used for coagulation. The tool is thus controlled in a precise manner with high dexterity in accordance with the surgeon manipulating a handheld controller. Some functions of the system such as control of the energy emitter may be assigned to a foot pedal controller that the surgeon manipulates with their foot.

SUMMARY

An embodiment of the invention is directed to a foot pedal assembly (or system) for controlling a robotic surgical system, with integrated foot presence sensing. The foot pedal assembly may include a foot pedal with a foot presence sensor (or multiple sensors) built into the cover portion of the pedal. More specifically, in one embodiment, a sensor such as a proximity sensor may be built directly into the pedal. The proximity sensor may be used to detect the presence of a user's foot prior to the foot contacting a particular pedal (e.g., hovering). In this aspect, the system can notify the user their foot is over a pedal, about to press a given pedal, moving toward a pedal, or provide other similar information relating to the user's foot position with respect to the pedal individually. In addition, in some cases, the foot pedal assembly includes a number of foot pedals having sensors incorporated therein, so that the presence of a foot with respect to each of the pedals individually can be determined. This information can be used by the user and/or system to, for example, prevent unintentional pedal activation, anticipate a surgical operation and prepare the corresponding instrument, and/or determine a motion or speed of the foot. For example, when one pedal is active and the foot is detected over another pedal, the user can be notified and/or the other pedal deactivated to prevent unintentional activation. The hardware therefore allows for higher precision in notifying the user of the location of her/his foot prior to activation of any particular pedal. More specifically, the system achieves presence sensing of a foot over any given pedal individually so that a user can be alerted.

Representatively, in one embodiment, the invention may include an assembly of pedals and associated software for running algorithms, processing operations, processes, or the like, to optimize performance and user experience in applying the pedals with integrated presence (or hover) sensing. For example, in one aspect, the assembly may include a layout, arrangement or array of seven pedals. There may be three pedals arranged on the left half of the layout and four pedals arranged on the right half of the layout, at known positions. One or more of the four pedals arranged together on the right half may be used to activate energy or advanced tool functionality (e.g., laser, stapler, etc.), while the pedals on the left half may be used to operate cameras and/or switch instruments. Since notifications with respect to energy pedals may be important, each of the four pedals on the right half layout may have sensors built therein, although sensors may be built into all seven pedals, or any combination of pedals where presence sensing is desired.

The integration of the sensors into the pedals as discussed herein may have several additional applications. For example, pedal prioritization can be implemented based on the information obtained by the sensors. For example, when a user places their foot on an upper pedal, both the upper pedal and lower pedal sensors may be triggered (the user's foot overlaps both pedals). The system, however, can prioritize which pedal the system should alert the user about based on the function of the particular pedal. For example, the system knows that upper pedals map to energy functions, which if activated unintentionally, may be more undesirable than an inadvertent activation of any of the lower pedals. In this scenario, although hover is detected over both pedals, the system alerts the user of the hover over the upper pedal, since unintentional activation of this pedal will result in more harm.

In addition, by having two sensors placed a known distance apart, the system can detect foot motion and speed when, for example, two or more sensors are detected in sequence. For example, it can be determined that the user's foot is moving from the floor (no sensors triggered), toward a first pedal (first pedal sensor triggered), and then on to a second pedal (second pedal sensor triggered). This motion (and speed) knowledge can assist in providing the user with critical information about results of any action they're about to take and also assist in optimizing operations.

Still further, in one aspect, integrating sensors into the pedals on the left and/or right side layout may assist with training surgeons new to the system how to use the system, or to optimize performance on the system. Representatively, it is known that there is a correlation between procedure time and number of camera clutches. Therefore, if the system can inform a user that their feet are unnecessarily resting on the camera clutch pedal, this procedure variable can be optimized. In addition, when sensors are built into all seven pedals, the system may be configured to toggle on/off the left pedal sensors, or alter the size or frequency of the hover-related notifications.

More specifically, in one embodiment, the invention is directed to a foot pedal assembly for controlling a robotic surgical system. The foot pedal assembly including a foot pedal base, a foot pedal and a sensor built into the foot pedal. The foot pedal may be movably coupled to the foot pedal base, such that it moves with respect to the base, and have a contact surface extending from a distal end to a proximal end of the foot pedal. The sensor coupled to the contact surface of the foot pedal at a position closer to the proximal end than the distal end, the sensor is operable to sense a target object positioned a distance over the contact surface. In some cases, the foot pedal may pivot around an axle coupled to the foot pedal base. The axle may be positioned closer to the distal end than the proximal end, and the sensor may be closer to the proximal end than the axle. Still further, the sensor may be coupled to the contact surface at a position that is between the distal end and a point midway between the distal end and the proximal end. In addition, a cavity may be formed through the contact surface, and the sensor may be mounted within the cavity. In some embodiments, the sensor may be an optical sensor having an emitter and a detector, and the emitter emits a beam of electromagnetic radiation in a direction away from the contact surface. In other cases, the sensor may be a capacitive sensor. Still further, the sensor may be one of an array of sensors coupled to the contact surface of the foot pedal. In addition, the foot pedal assembly may be one of an array of foot pedal assemblies operable to control different surgical robotic operations. In addition, the assembly may include a foot pedal assembly platform having an upper platform and a lower platform to which the array of foot pedal assemblies are mounted. In some cases, a larger number of the foot pedal assemblies in the array of foot pedal assemblies are mounted to the upper platform than the lower platform of the foot pedal assembly platform.

In another embodiment, the invention is directed to a foot pedal system including a foot pedal assembly platform, a first foot pedal assembly and a second foot pedal assembly coupled to the foot pedal assembly platform, and a processor. Each of the first foot pedal assembly and the second foot pedal assembly may have a foot pedal movably coupled to a foot pedal base and an optical sensor coupled to a contact surface of the foot pedal that faces away from the foot pedal base. The optical sensor may be operable to emit a light beam in a direction away from the contact surface and detect a presence of a target object prior to activation of the first foot pedal assembly or the second foot pedal assembly by the target object. The processor may be configured to determine a position of the target object with respect to the first foot pedal assembly or the second foot pedal assembly based on the presence detected by the optical sensor coupled to the first foot pedal assembly or the second foot pedal assembly. In some embodiments, the optical sensor may be positioned closer to a proximal end of the contact surface than a distal end of the contact surface. In addition, the processor may further be configured to determine whether the target object is positioned closer to the proximal end of the contact surface than the distal end of the contact surface based on the presence detected by the optical sensor. The optical sensor may be one of an array of optical sensors coupled to different regions of the contact surface of a respective foot pedal, and the processor may further be configured to determine the target object is aligned with one of the different regions. The processor may also be configured to determine the target object is over the contact surface of the first foot pedal assembly prior to the target object contacting the contact surface of the first foot pedal assembly based on the presence of the target object being detected by the optical sensor of the first foot pedal assembly. In some cases, the processor may be configured to determine the position of the target object with respect to the first foot pedal assembly based on the presence of the target object being detected by the optical sensor of the second foot pedal assembly. The processor may further be configured to determine a lateral motion of the target object when the presence of the target object is detected by the optical sensors in sequence. Still further, the processor is further configured to alert a user that the presence of the target object is detected over one of the first foot pedal assembly or the second foot pedal assembly when the other of the first foot pedal assembly or the second foot pedal assembly is actively controlling a robotic operation. In addition, the processor may be configured to prevent activation of the first foot pedal assembly when the presence of the target object is detected over the first foot pedal assembly while the second foot pedal assembly is actively controlling a robotic operation. In some cases, the first foot pedal assembly is operable to control a first surgical robotic operation and the second foot pedal assembly is operable to control a second surgical robotic operation that is different than the first surgical robotic operation. The first surgical robotic operation may include an energy device and the second surgical robotic operation my include a non-energy instrument. In addition, the foot pedal assembly platform may include an upper platform and a lower platform, and the first foot pedal assembly is coupled to the upper platform and the second foot pedal assembly is coupled to the lower platform.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The embodiments of the invention are illustrated by way of example and not by way of limitation in the figures of the accompanying drawings in which like references indicate similar elements. It should be noted that references to "an" or "one" embodiment of the invention in this disclosure are not necessarily to the same embodiment, and they mean at least one. Also, in the interest of conciseness and reducing the total number of figures, a given figure may be used to illustrate the features of more than one embodiment of the invention, and not all elements in the figure may be required for a given embodiment.

DETAILED DESCRIPTION

Several embodiments of the invention with reference to the appended drawings are now explained. Whenever the shapes, relative positions and other aspects of the parts described in the embodiments are not explicitly defined, the scope of the invention is not limited only to the parts shown, which are meant merely for the purpose of illustration. Also, while numerous details are set forth, it is understood that some embodiments of the invention may be practiced without these details. In other instances, well-known circuits, structures, and techniques have not been shown in detail so as not to obscure the understanding of this description.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

The terms "or" and "and/or" as used herein are to be interpreted as inclusive or meaning any one or any combination. Therefore, "A, B or C" or "A, B and/or C" mean "any of the following: A; B; C; A and B; A and C; B and C; A, B and C." An exception to this definition will occur only when a combination of elements, functions, steps or acts are in some way inherently mutually exclusive.

In addition, the phrase "configured to," as used herein, may be interchangeable with, or otherwise understood as referring to, for example, a device that is "suitable for", "having the capacity to", "designed to", "adapted to", "made to", or otherwise "capable of" operating together with another device or other components. For example, a "processor configured to perform A, B, and C" may refer to a processor (e.g., a central processing unit (CPU) or an application processor) that may perform operations A, B and C by executing one or more software programs which stores a dedicated processor (e.g., an embedded processor) for performing a corresponding operation.

Figure 1:
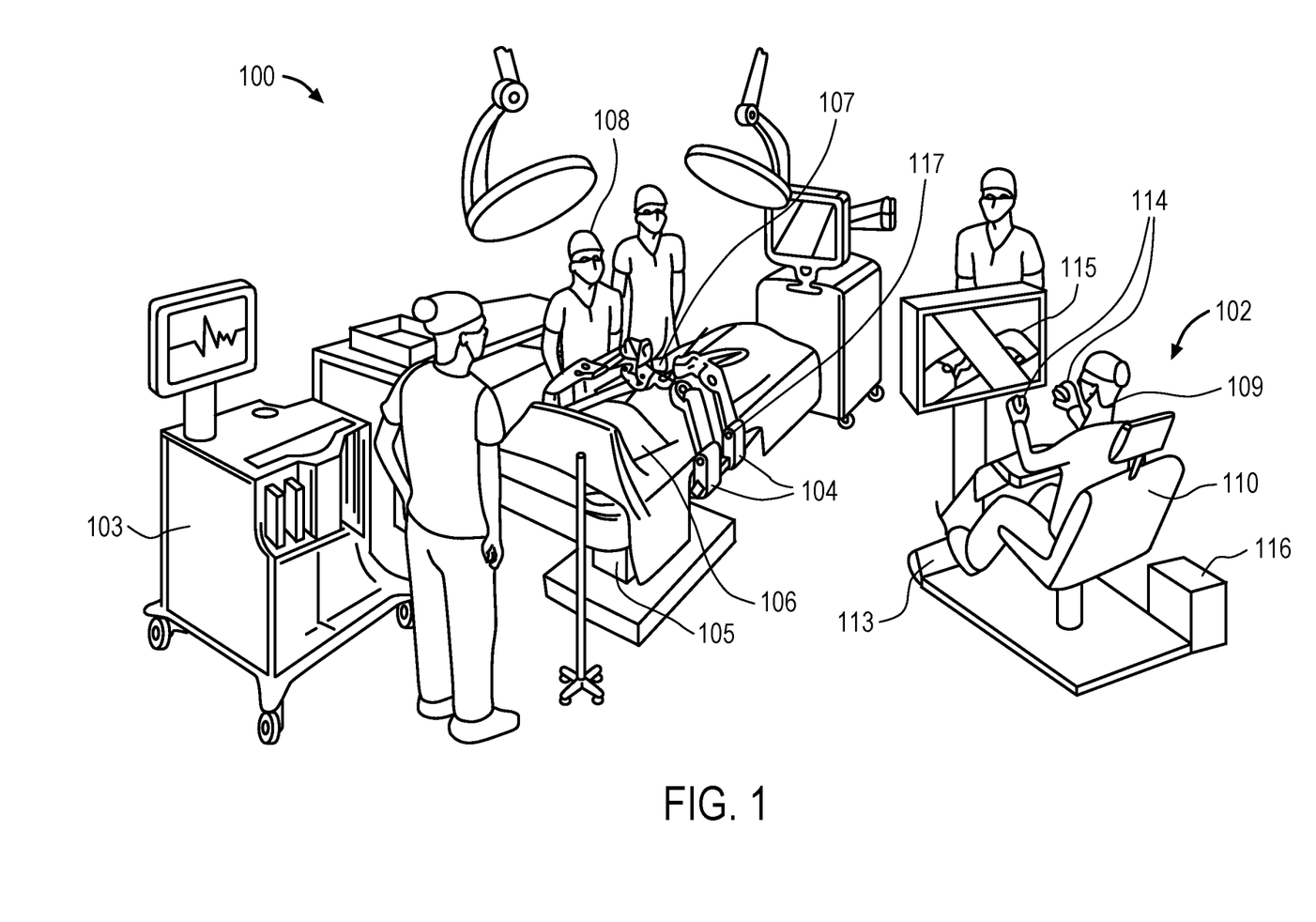
FIG. 1 is a pictorial view of one embodiment of a surgical system in an operating arena.

Referring to FIG. 1, FIG. 1 illustrates a pictorial view of an example surgical system 100 in an operating arena. The robotic surgical system 100 includes a user console 102, a control tower 103, and one or more robotic surgical arms 104 at a surgical platform 105, e.g., a table, a bed, etc. The robotic surgical system 100 can incorporate any number of devices, tools, or accessories used to perform surgery on a patient 106. For example, the robotic surgical system 100 may include one or more surgical tools 7 used to perform surgery. A surgical tool 107 may be an end effector that is attached to a distal end of a surgical arm 104, for executing a surgical procedure.

Each surgical tool 107 may be manipulated manually, robotically, or both, during the surgery. For example, the surgical tool 107 may be a tool used to enter, view, or manipulate an internal anatomy of the patient 106. In an embodiment, the surgical tool 107 is a grasper that can grasp tissue of the patient. The surgical tool 107 may be controlled manually, by a bedside operator 108; or it may be controlled robotically, via actuated movement of the robotic surgical arm 104 to which it is attached. The robotic surgical arms 104 are shown as a table-mounted system, but in other configurations the surgical arms 104 may be mounted in a cart, ceiling or sidewall, or in another suitable structural support.

Generally, a remote operator 109, such as a surgeon or other operator, may use the user console 102 to remotely manipulate the surgical arms 104 and/or the attached surgical tools 107, e.g., teleoperation. The user console 102 may be located in the same operating room as the rest of the robotic surgical system 100, as shown in FIG. 1. In other environments however, the user console 102 may be located in an adjacent or nearby room, or it may be at a remote location, e.g., in a different building, city, or country. The user console 102 may comprise a seat 110, foot-operated controls 113, one or more handheld user interface devices, UID 114, and at least one user display 115 that is configured to display, for example, a view of the surgical site inside the patient 106. In the example user console 102, the remote operator 109 is sitting in the seat 110 and viewing the user display 115 while manipulating a foot-operated control 113 and a handheld UID 114 in order to remotely control the surgical arms 104 and the surgical tools 107 (that are mounted on the distal ends of the surgical arms.)

In some variations, the bedside operator 108 may also operate the robotic surgical system 100 in an "over the bed" mode, in which the beside operator 108 (user) is now at a side of the patient 106 and is simultaneously manipulating a robotically-driven tool (end effector as attached to the surgical arm 104), e.g., with a handheld UID 114 held in one hand, and a manual laparoscopic tool. For example, the bedside operator's left hand may be manipulating the handheld UID to control a robotic surgical component, while the bedside operator's right hand may be manipulating a manual laparoscopic tool. Thus, in these variations, the bedside operator 108 may perform both robotic-assisted minimally invasive surgery and manual laparoscopic surgery on the patient 106.

During an example procedure (surgery), the patient 106 is prepped and draped in a sterile fashion to achieve anesthesia. Initial access to the surgical site may be performed manually while the arms of the robotic surgical system 100 are in a stowed configuration or withdrawn configuration (to facilitate access to the surgical site.) Once access is completed, initial positioning or preparation of the robotic surgical system 100 including its arms 104 may be performed. Next, the surgery proceeds with the remote operator 109 at the user console 102 utilizing the foot-operated controls 113 and the UIDs 114 to manipulate the various end effectors and perhaps an imaging system to perform the surgery. Manual assistance may also be provided at the procedure bed or table, by sterile-gowned bedside personnel, e.g., the bedside operator 108 who may perform tasks such as retracting tissues, performing manual repositioning, and tool exchange upon one or more of the surgical arms 104. Non-sterile personnel may also be present to assist the remote operator 109 at the user console 102. When the procedure or surgery is completed, the robotic surgical system 100 and the user console 102 may be configured or set in a state to facilitate post-operative procedures such as cleaning or sterilization and healthcare record entry or printout via the user console 102.

In one embodiment, the remote operator 109 holds and moves the UID 114 to provide an input command to move a robot arm actuator 117 in the robotic surgical system 100. The UID 114 may be communicatively coupled to the rest of the robotic surgical system 100, e.g., via a console computer system 116. The UID 114 can generate spatial state signals corresponding to movement of the UID 114, e.g. position and orientation of the handheld housing of the UID, and the spatial state signals may be input signals to control a motion of the robot arm actuator 117. The robotic surgical system 100 may use control signals derived from the spatial state signals, to control proportional motion of the actuator 117. In one embodiment, a console processor of the console computer system 116 receives the spatial state signals and generates the corresponding control signals. Based on these control signals, which control how the actuator 117 is energized to move a segment of the arm 104, the movement of a corresponding surgical tool that is attached to the arm may mimic the movement of the UID 114. Similarly, interaction between the remote operator 109 and the UID 114 can generate for example a grip control signal that causes a jaw of a grasper of the surgical tool 107 to close and grip the tissue of patient 106.

Robotic surgical system 100 may include several UIDs 114, where respective control signals are generated for each UID that control the actuators and the surgical tool (end effector) of a respective arm 104. For example, the remote operator 109 may move a first UID 114 to control the motion of an actuator 117 that is in a left robotic arm, where the actuator responds by moving linkages, gears, etc., in that arm 104. Similarly, movement of a second UID 114 by the remote operator 109 controls the motion of another actuator 117, which in turn moves other linkages, gears, etc., of the robotic surgical system 100. The robotic surgical system 100 may include a right surgical arm 104 that is secured to the bed or table to the right side of the patient, and a left surgical arm 104 that is at the left side of the patient. An actuator 117 may include one or more motors that are controlled so that they drive the rotation of a joint of the surgical arm 104, to for example change, relative to the patient, an orientation of an endoscope or a grasper of the surgical tool 107 that is attached to that arm. Motion of several actuators 117 in the same arm 104 can be controlled by the spatial state signals generated from a particular UID 114. The UIDs 114 can also control motion of respective surgical tool graspers. For example, each UID 114 can generate a respective grip signal to control motion of an actuator, e.g., a linear actuator, that opens or closes jaws of the grasper at a distal end of surgical tool 107 to grip tissue within patient 106.

In some aspects, the communication between the surgical platform 105 and the user console 102 may be through a control tower 103, which may translate user commands that are received from the user console 102 (and more particularly from the console computer system 116) into robotic control commands that transmitted to the arms 104 on the surgical platform 105. The control tower 103 may also transmit status and feedback from the surgical platform 105 back to the user console 102. The communication connections between the surgical platform 105, the user console 102, and the control tower 103 may be via wired and/or wireless links, using any suitable ones of a variety of data communication protocols. Any wired connections may be optionally built into the floor and/or walls or ceiling of the operating room. The robotic surgical system 100 may provide video output to one or more displays, including displays within the operating room as well as remote displays that are accessible via the Internet or other networks. The video output or feed may also be encrypted to ensure privacy and all or portions of the video output may be saved to a server or electronic healthcare record system.

Figure 2:
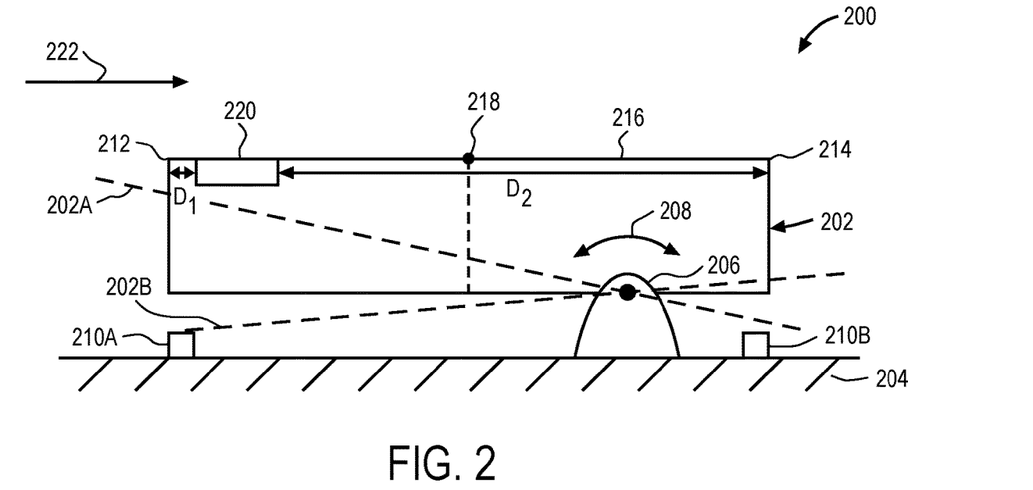
FIG. 2 is a side view of an embodiment of a foot pedal assembly.

A foot-operated control including a foot pedal assembly or system having an integrated sensor for sensing the presence and/or location of a user's foot on the foot-operated control will now be described. Referring now to FIG. 2, FIG. 2 illustrates a side view of one example of a foot pedal assembly 200 that can be used to control, or otherwise actuate, a robotic operation of the robotic surgical system 100 (e.g., an operation of the robotic surgical arm 104). Foot pedal assembly 200 may include a foot pedal 202 that is movably coupled to a foot pedal base 204. The term "foot pedal" is generally intended to refer to any type of foot-operated lever that can be used to control the robotic operation. The foot pedal base 204 may be any type of structure suitable for supporting the pedal. In addition, it should be understood that while a "foot pedal" and "foot pedal base" are described and shown herein in the context of a foot, the pedal and base should be understood to cover any sort of lever and support member assembly that can be used in a similar manner by any body part, machine, robotic assembly, or the like to actuate or otherwise control a surgical robotic operation (or other operations requiring a pedal and base assembly).

In some cases, the foot pedal 202 may be rotatably coupled to the foot pedal base 204, while in other cases, the foot pedal 202 may be, for example, a floating pedal that remains relatively parallel to the base 204, and moves up and down. FIG. 2 illustrates an embodiment where the foot pedal 202 is rotatably coupled to the foot pedal base 204. Representatively, foot pedal 202 and/or foot pedal base 204 include an axle 206 around which foot pedal 202 rotates or pivots as shown by arrow 208. Rotation of foot pedal 202 around axle 206 moves foot pedal 202 from a "neutral" position in which it is substantially horizontal, or otherwise parallel to foot pedal base 204, to different "active" positions 202A, 202B in which it is at an angle with respect to foot pedal base 204 (as illustrated by dashed lines). The foot pedal 202 may be considered to be in a "neutral" position when it is not causing, actuating, or otherwise controlling, a robotic operation (e.g. an operation of the robotic surgical arm 104). On the other hand, positions 202A, 202B of foot pedal 202 are considered "active" because in these positions, foot pedal 202 is causing, actuating, or otherwise controlling, a robotic operation (e.g., an operation of the robotic surgical arm 104). For example, in positions 202A, 202B, foot pedal 202 may contact one or more of switches 210A and 210B, which, in turn, send a signal to a control system (e.g., a console processor of the console computer system 116) to actuate, or otherwise control, the robotic operation. In this aspect, foot pedal 202 may be referred to herein as being "active", "activated" or "actuated" when in positions 202A, 202B (e.g., a position achieved when a user's foot presses on the pedal), and "neutral" or "inactive" when in the horizontal position (e.g., the resting position prior to the user's foot contacting the pedal).

Referring now in more detail to foot pedal 202, foot pedal 202 may include a proximal portion or end 212 and a distal portion or end 214, and a contact surface 216 extending between the two portions or ends 212, 214. During operation, the proximal portion 212 will be near the heel of the foot, and the distal portion 214 will be farther from the heel (e.g., closer to the toe). The contact surface 216 may be a substantially flat or planar surface that, in the neutral pedal position, may be substantially parallel to, and face away from, base portion 204. On the other hand, in the active pedal position (e.g., when a user's foot contacts surface 216), contact surface 216 may be rotated such that it is at an angle with respect to base portion 204. Contact surface 216 may be referred to as a "contact" surface herein because this is the portion of foot pedal 202 which is contacted by the user's foot to activate the pedal assembly such as by rotating, or otherwise moving, foot pedal 202. For example, foot pedal 202 may be manually moved (e.g., rotate, pivot, move up/down) with respect to foot pedal base 204 when a force or pressure is applied against surface 216. Therefore in this configuration, when a user's foot is positioned on surface 216 (e.g. to cause the pedal to rotate), the toes of the user's foot may be near distal end 214 (and used to rotate the distal end 214 toward switch 210B) and the heel may be positioned near proximal end 212 (and used to rotate the proximal end 212 toward switch 210A). In addition, it is noted that, in this embodiment, axle 206 is shown positioned closer to the distal end 214 than the proximal end 212 of foot pedal 202. In other embodiments, however, axle 206 may be located closer to the foot pedal mid point 218 than the distal end 214, closer to the mid point 218 than the proximal end 212 or closer to the proximal end 212 than the distal end 214, or anywhere between the proximal and distal ends 212, 214, respectively.

Foot pedal assembly 200 may further include a sensor 220. As previously discussed, foot pedal assembly 200 is used to control, or otherwise help to control, an operation of a surgical tool 107 (e.g., robotic arm 104) on a patient 106. In this aspect, it is particularly important that the pedal assembly not be accidentally, or otherwise inadvertently, activated (e.g. rotated or pressed) during, for example, another surgical operation being performed by the user (e.g., using another pedal assembly). In addition, in cases where multiple foot pedal assemblies are present, it is further important that a user be aware of which pedal they are about to press before activation of the pedal. Sensor 220 is therefore provided to detect a presence of the user's foot (also referred to herein as a target object), prior to the foot contacting surface 216 and activating assembly 200. In other words, to detect the user's foot hovering a distance over surface 216, but not yet contacting surface 216. In this aspect, it is particularly important that sensor 220 be mounted at a specific, and known, location on foot pedal 202 so that the foot presence can be immediately detected (e.g., before the foot is entirely over the pedal). In this aspect, sensor 220 may, in one embodiment, be mounted, attached, connected, or otherwise built into, an end of foot pedal 202. Representatively, when the pedal is oriented so that the user's foot slides on foot pedal 202 in a direction from left to right (as illustrated by arrow 222), sensor 220 may be positioned closer to proximal end 212 than distal end 214. For example, in some embodiments, sensor 220 may be positioned anywhere between proximal end 212 and mid point 218 of surface 216. Said another way, the distance ($D_1$) between sensor 220 and proximal end 212 is less than the distance ($D_2$) between sensor 220 and distal end 214. Still further, the position of sensor 220 may be defined with respect to axle 206. For example, where axle 206 is positioned closer to distal end 214 than proximal end 212 as shown, sensor 220 may be positioned closer to the proximal end 212 than axle 206.

Figure 3:
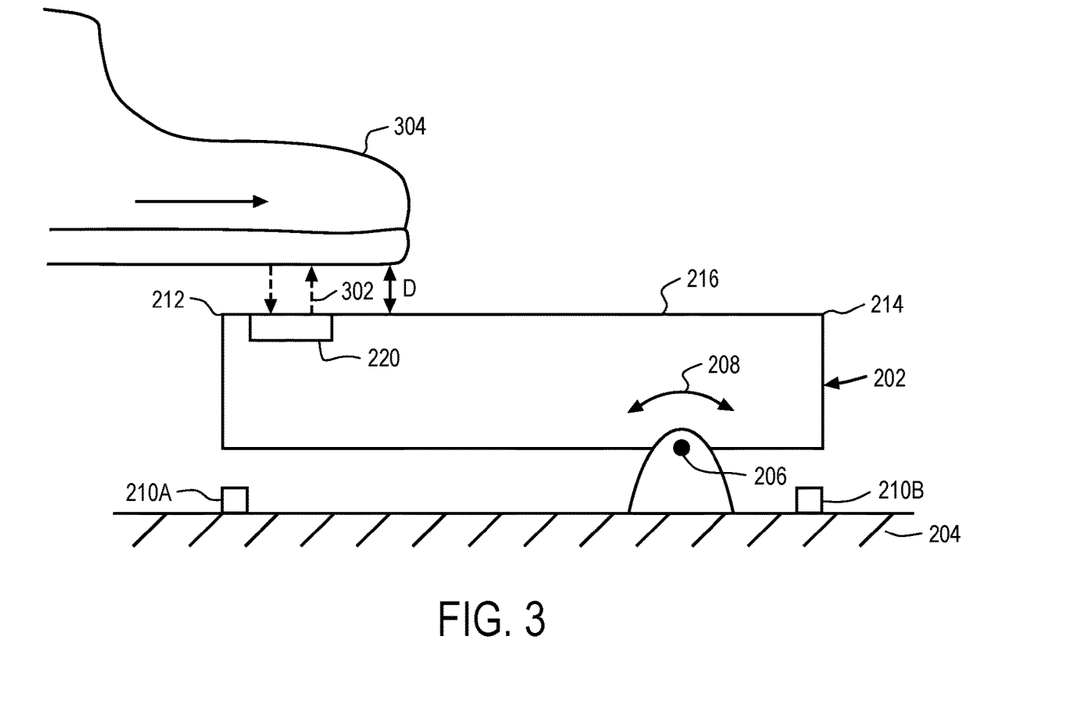
FIG. 3 is a side view of the foot pedal assembly of FIG. 2.

Referring now to sensor 220 in more detail, sensor may be any type of sensor suitable for detecting the presence of the user's foot 304 (or any target object) when the foot is spaced a distance (d) from surface 216 as shown in FIG. 3. In other words, the sensor 220 must be able to detect the foot presence when the foot 304 is positioned over contacting surface 216, and prior to, contacting surface 216 (e.g., prior to activation of assembly 200). Said another way, the sensor 220 detects the presence of foot 304 when it is positioned over surface 216, and above a plane of surface 216 and sensor 220. In this aspect, distance (d) may be understood to be any distance greater than zero. In addition, foot 304 may be considered over or above surface 216 (and sensor 220) in that it is positioned on a side of surface 216 opposite base portion 204. Moreover, foot 304 is positioned over, or otherwise aligned with, a sensing side, or face, of sensor 220. In some embodiments, sensor 220 may be an optical sensor such as a proximity sensor having an emitter that emits a beam of light (e.g., beam of electromagnetic or infrared radiation), and a detector that detects the beam reflected off the target object. The proximity sensor may be positioned with respect to surface 216 such that it emits the beam electromagnetic radiation in a direction away (as illustrated by arrow 302) from surface 216. For example, the electromagnetic radiation may be emitted in a direction substantially normal, or otherwise perpendicular to, a plane of surface 216. In other embodiments, sensor 220 may be positioned such that it emits radiation in any direction away from surface 216 so long as it is not parallel to surface 216. In the case of a proximity sensor, the presence or hovering of the foot 304 over surface 216 and/or sensor 220 may be considered detected when the sensor detector detects the beam 302 emitted by the emitter being reflected off of the foot 304, back to sensor 220. The absence of a reflected beam indicates there is no target object (e.g., foot 304) present. In addition, the sensor 220 can further be used to detect, indicate, or otherwise determine, the distance (d) of the target object 304 over surface 216. For example, the distance (d) can be determined based on an intensity of the light beam reflected back to the sensor 220. This information can be used to indicate how close the target object (e.g., foot 304) is to surface 216, and provide more specific information regarding whether the user is about to press, or otherwise contact, surface 216. In this aspect, in addition to sensing the presence of the foot 304 over surface 216 in general (e.g., the object is/is not detected), the sensor 220 can provide specific information that can be used to determine the position or location of the target object along an x, y and z-axis (or plane), with respect to surface 216. Although a proximity sensor is disclosed, in some embodiments, sensor 220 may be any type of sensor that can detect an object without physical contact between the sensor 220 (or a surface to which it is mounted) and the target object. For example, in some embodiments, sensor 220 may be a capacitive sensor that is capable of detecting an object within a distance (d) range of from about 30 mm to 50 mm.

In addition, it should be further emphasized that because sensor 220 is built directly into the foot pedal 202, the presence (or hovering) of the foot with respect to that particular pedal can be more precisely detected than, for example, where a sensor is positioned near (but not attached to) the pedal, or multiple pedals. In particular, where the sensor is instead built into a structure that is near the pedal or multiple pedals, the system may be more likely to detect false positives (a foot is sensed but is not actually on the pedal) or false negatives (the foot is not sensed but is actually on the pedal).

Figure 4:
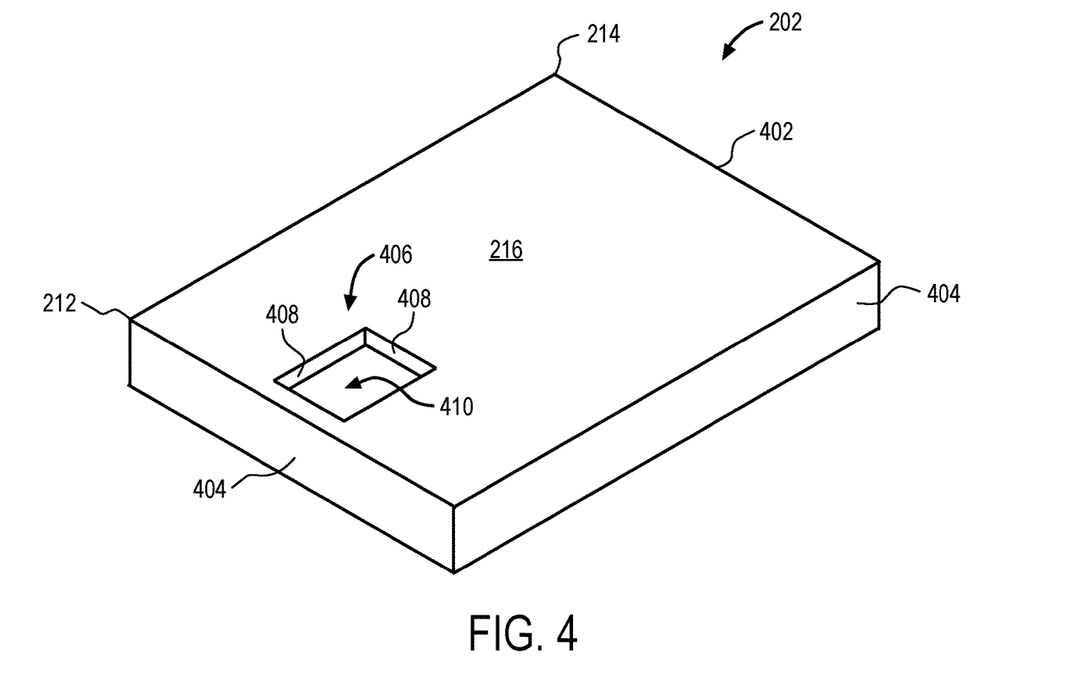
FIG. 4 is a top perspective view of an embodiment of a foot pedal.
Figure 5:
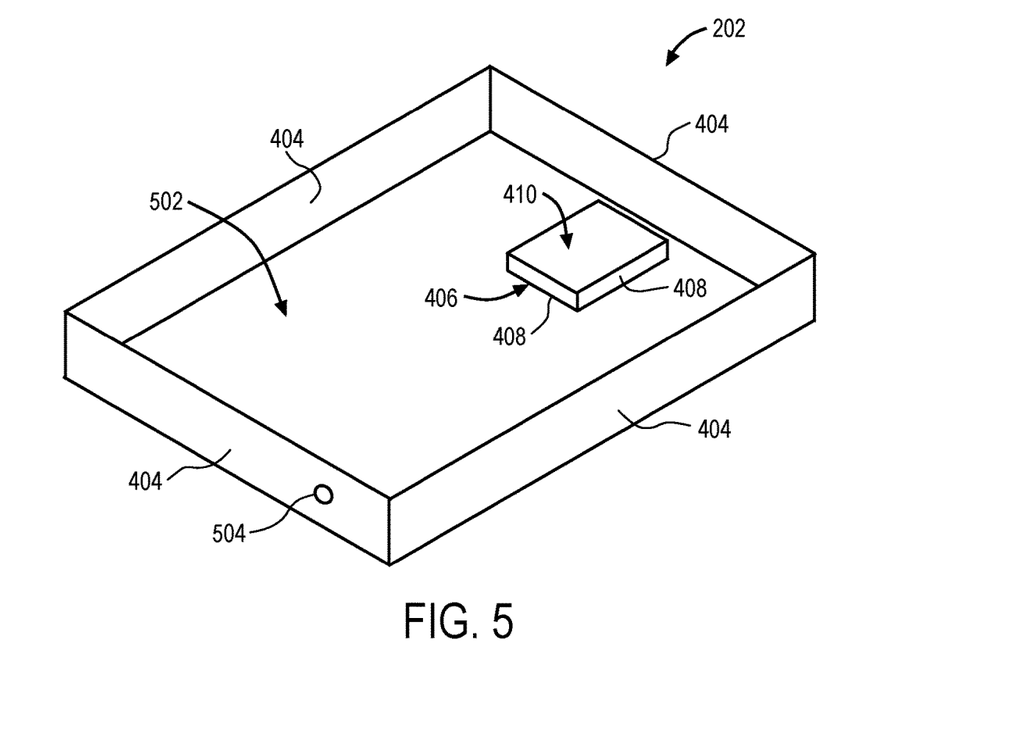
FIG. 5 is a bottom perspective view of an embodiment of the foot pedal of FIG. 4.

Referring now to FIG. 4-FIG. 7, FIG. 4-FIG. 7 illustrate perspective views of one embodiment of a sensor built into a foot pedal. Representatively, FIG. 4 illustrates a top perspective view of foot pedal 202, and FIG. 5 illustrates the bottom perspective view of foot pedal 202 shown in FIG. 4. From these views, it can be seen that foot pedal 202 may include a housing or cover 402 which includes surface 216 (e.g., surface 216 may be a top surface of a top wall forming cover 402) and sidewalls 404. Sidewalls 404 surround surface 216 (e.g., the top wall forming surface 216), and extend perpendicular to surface 216, such that the combination of structures forms a relatively hollow chamber 502 (see FIG. 5) along the bottom side of pedal 202. It should be noted that the bottom side of pedal 202 having chamber 502 as shown in FIG. 5, would be the side facing the foot pedal base 204 as described in FIG. 2 and FIG. 3, and therefore cover, enclose or house any interior components of the assembly.

In some cases, cover 402 includes four sidewalls 404, and two of the sidewalls may be longer than two of the other sidewalls such that cover 402 has a substantially rectangular shape. Sensor 220 may, in some embodiments, be closer to one of the shorter sidewalls (or ends of cover 402), than the longer sidewalls. Other cover sizes and shapes are, however, contemplated (e.g., square, rectangular, elongated, elliptical, circular, semi-circular, or the like). In addition, although not shown, in some embodiments, portions of sidewalls 404 may be dimensioned (e.g., curve downward or protrude) and the axle (axle 206 as previously discussed in connection with FIG. 1 and FIG. 2) inserted through opposing sidewalls (e.g., across cover 402 through opposite sidewalls). In addition, in some embodiments, a port 504 may be formed through one of sidewalls 404 to accommodate circuitry running through cover 402.

Figure 6:
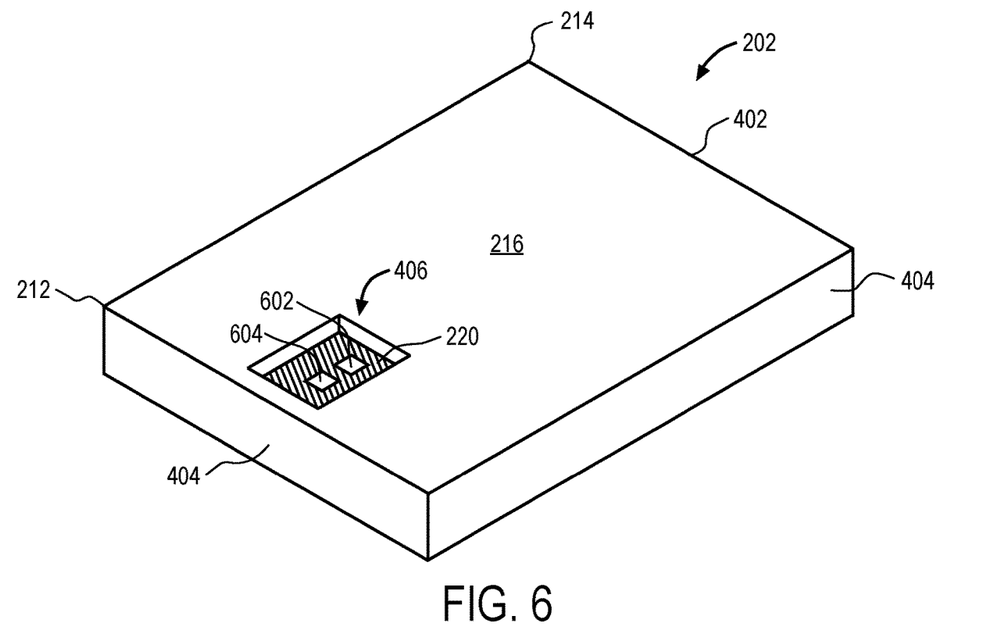
FIG. 6 is a top perspective view of an embodiment of the foot pedal of FIG. 4 with a sensor built therein.
Figure 7:
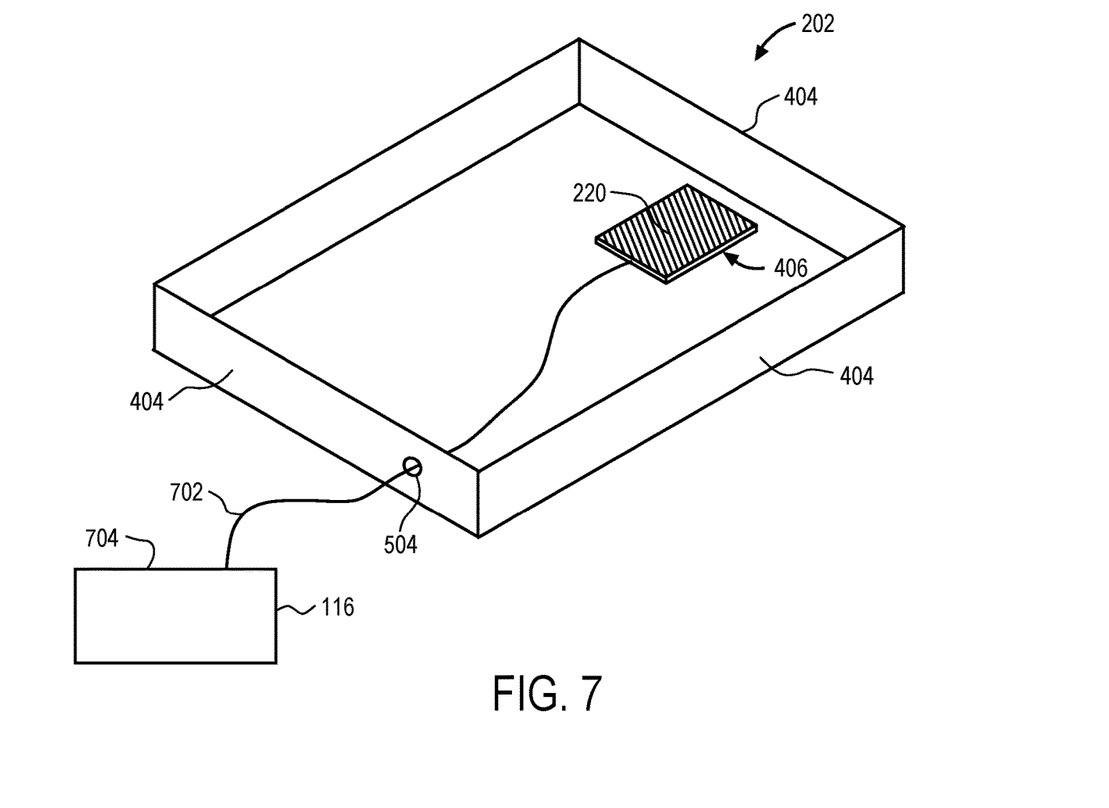
FIG. 7 is a bottom perspective view of an embodiment of the foot pedal of FIG. 4 with a sensor built therein.

Cover 402 may further include a channel or cavity 406 extending below surface 216 (e.g., into chamber 502). Cavity 406 may include interior sidewalls 408 that are coupled to an opening 410 through surface 216, and therefore define a channel extending below surface 216. In some cases, cavity 406 may be open at both ends as shown. In other cases, however, the cavity 406 could have a closed bottom (e.g., be closed at an end opposite surface 216). Cavity 406 is dimensioned to receive sensor 220 as shown in FIG. 6 and FIG. 7. In particular, FIG. 6 and FIG. 7 are perspective top and bottom views, respectively, showing sensor 220 positioned, connected, or mounted (e.g., screwed) within cavity 406. For example, sensor 220 could be screwed to one or more of sidewalls 408 or directly to the top wall forming surface 216. From these views it can be seen that when sensor 220 is mounted, or otherwise positioned within cavity 406, the emitter 602 and detector 604 are arranged to detect the presence of an object positioned over, or hovering above, surface 216. In particular, emitter 602 is oriented such that it emits a beam of light in a direction away from surface 216, as previously discussed in reference to FIG. 3. It should further be understood that in some embodiments, emitter 602 and detector 604 of sensor 220 may be within a same plane as surface 216, or may actually be below surface 216 such that the beam output by emitter 602 first passes through a plane of surface 216 and then in a direction away from surface 216. In addition, it can also be seen that any circuitry, such as wiring 702 necessary to operate sensor 220 runs through cover 402 via port 504. For example, wiring 702 may run from sensor 220 to a processor 704 associated with computer 116 (discussed in reference to FIG. 1). Processor 704 may, in turn, based on the information detected by sensor 220 (e.g., presence of a target object), determine a position of the target object with respect to a single pedal assembly, another pedal assembly, a motion of the target object, a speed of the target object, or the like. For example, where it is known that sensor 220 is closer to the proximal end 212 than distal end 214 of foot pedal 202, and the presence of the target object is detected by sensor 220, processor 704 may determine that the target object is closer to the proximal end than the distal end. The processor 704 may further determine based on this information, or otherwise anticipate, that the user is about to activate foot pedal 202 to activate the corresponding robotic operation.

Figure 8:
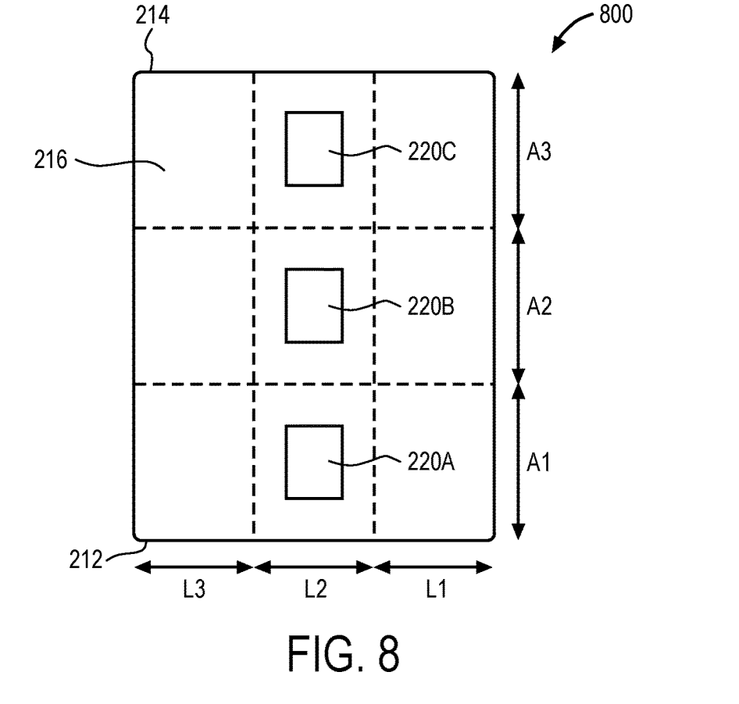
FIG. 8 is a top plan view of one embodiment of a foot pedal.
Figure 9:
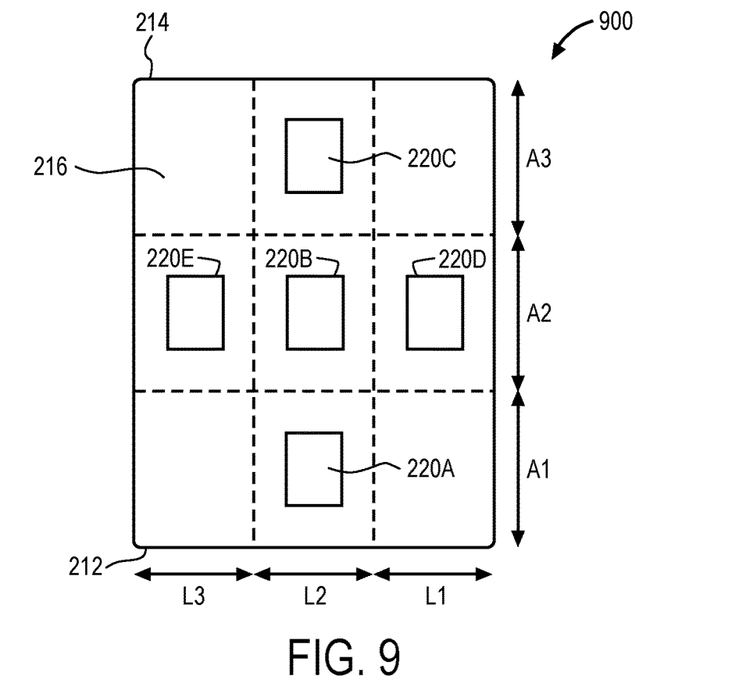
FIG. 9 is a top plan view of another embodiment of a foot pedal.
Figure 10:
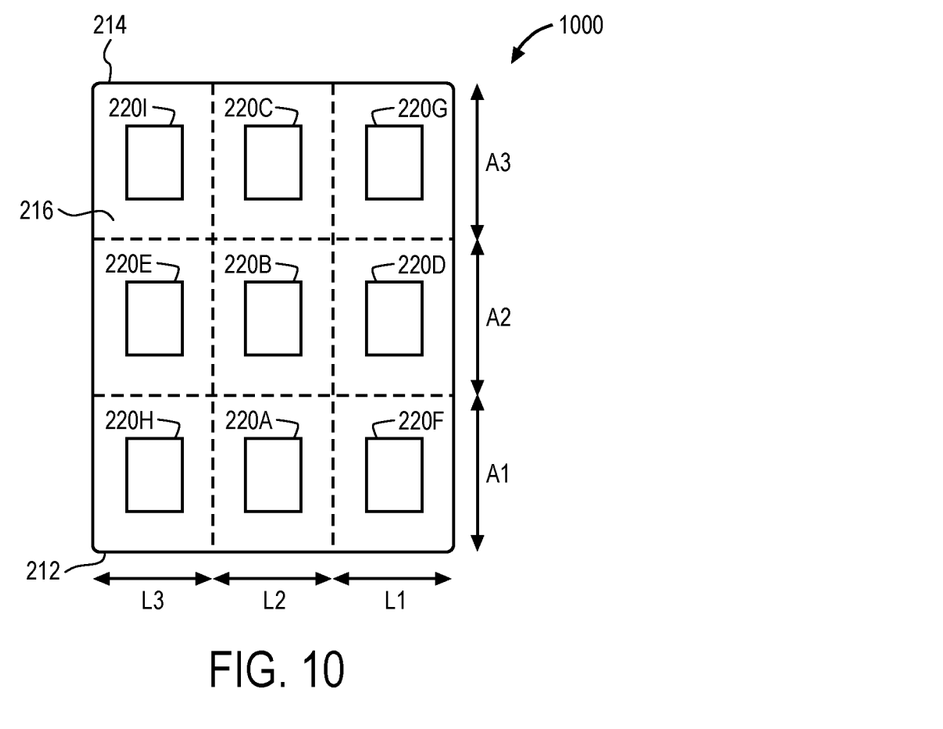
FIG. 10 is a top plan view of another embodiment of a foot pedal.

In addition, it is contemplated that in still further embodiments, a foot pedal could have an array of sensors built therein so that a position of the target object (e.g., the user's foot) with respect to the foot pedal (or perhaps an adjacent foot pedal) can be more precisely determined. Representatively, FIG. 8 to FIG. 10 illustrate top plan views of representative foot pedals having different sensor arrays. In particular, FIG. 8 illustrates an embodiment of a foot pedal 800 having a contact surface 216 extending between the proximal end 212 and the distal end 214, as previously discussed. In this embodiment, however, an array of three sensors 220A, 220B and 220C are located at different positions along contact surface 216. Representatively, sensor 220A is positioned near the proximal end 212, sensor 220C is positioned near the distal end 214 and sensor 220B is positioned between sensors 220A, 220C. The locations, or positions, of sensors 220A-220C along surface 216, and with respect to one another is known. Therefore, when one or more of the sensors 220A-220C detects a target object, the position or location of the target object over foot pedal 800, can also be determined. For example, 220A, 220B and 220C may be arranged with respect to known lateral positions (L1, L2 or L3) and known axial positions (A1, A2 or A3), which correspond to different regions or locations along surface 216 (along the x and y axis, respectively). In this aspect, if the target object is detected by sensor 220A at position L1,A1, or within a region defined by $L_1,A_1$ coordinates, it may be determined that the target object is near the proximal end 212 of surface 216. In addition, if the target object is simultaneously not detected by sensors 220B and 220C, it may be determined that the target object is only near proximal end 212 (e.g., is only partially over pedal 800). In other words, the user has just slid their foot over pedal 800 and may or may not intend to press pedal 800. On the other hand, if both of sensors 220A and 220B, or all three sensors 220A, 220B and 220C, detect the presence of a target object, it may be determined that the target object is entirely over pedal 800. In other words, the user's foot is completely over surface 216 and it is likely that the user intends to press pedal 800. Moreover, sensor 220 may further detect the distance of the foot from surface 216, and in turn the foot position in the z-axis, to further determine whether the user is about to press pedal 800, or otherwise contact surface 216, as previously discussed.

In addition to determining the position or location of the object (in the x, y and/or z-axis) using the array of sensors, a motion and/or speed of the object may further be determined. For example, in addition to the location of each of sensors 220A-220C being known, the distance between each of sensors 220A-220C is also known. Therefore, when the presence of the target object is detected sequentially by sensors 220A, 220B and/or 220C the direction that the target object and/or speed of the object movement across pedal 800 can also be determined. For example, if the target object is first detected by sensor 220A, followed by sensor 220B, and then sensor 220C, it can be determined that the target object is moving in an axial direction, toward distal end 214.

FIG. 9 and FIG. 10 illustrate further sensor arrays arranged on the foot pedal. In particular, FIG. 9 illustrates an embodiment of a foot pedal 900, similar to foot pedal 800, except that in addition to sensors 220A-220C arranged as previously discussed, foot pedal 900 includes additional sensors 220D and 220E. Sensors 220D and 220E are at a same axial position, A2, as sensor 220B, however, occupy lateral positions L1 and L3, respectively, along surface 216. In this aspect, additional information relating to the position, movement and/or speed of the target object can be determined. For example, the detection of the target object by sensor 220D or sensor 220E, or sequentially by sensor 220D then 220E, may be used to determine that the target object is near one side or the other of the pedal 800, or moving laterally toward one side or the other of the pedal 800. Similarly, FIG. 10 illustrates a foot pedal 1000 in which in addition to the previously discussed arrangement of sensors 220A-220E, sensors 220F, 220G, 220H and 220I are included. Sensors 220E-220I may occupy the remaining lateral and axial regions or positions (e.g., L1,A1; L1,A3; L3,A1; and L3,A3) such that additional position, motion and speed information of the target object may be determined as previously discussed.

Figure 11:
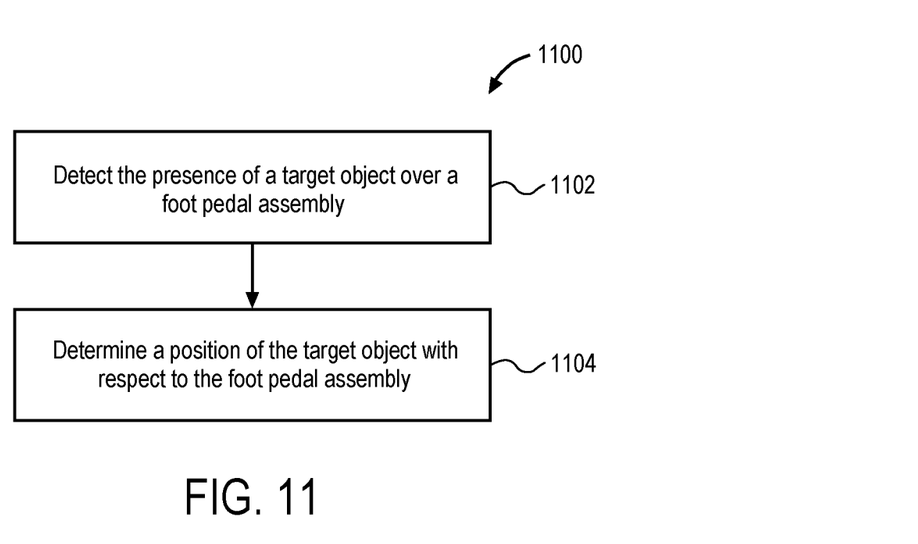
FIG. 11 is a flow chart of one embodiment of a process for determining a position of a target object.

FIG. 11 illustrates one embodiment of a process flow 1100 for determining an object position, as previously discussed. Representatively, as previously discussed, the presence of the target object over a foot pedal assembly (or foot pedal) is detected by a sensor (block 1102). The foot pedal may include a single sensor as previously discussed in reference to FIG. 1-FIG. 7, or could include an array of sensors as discussed in reference to FIG. 8-FIG. 10. A position of the target object with respect to the foot pedal assembly can then be determined based on the detection of the object presence by the sensor (block 1104). In addition, as previously discussed, depending on the number of sensors and their arrangement, a motion and/or speed of the target object may further be determined.

Figure 12:
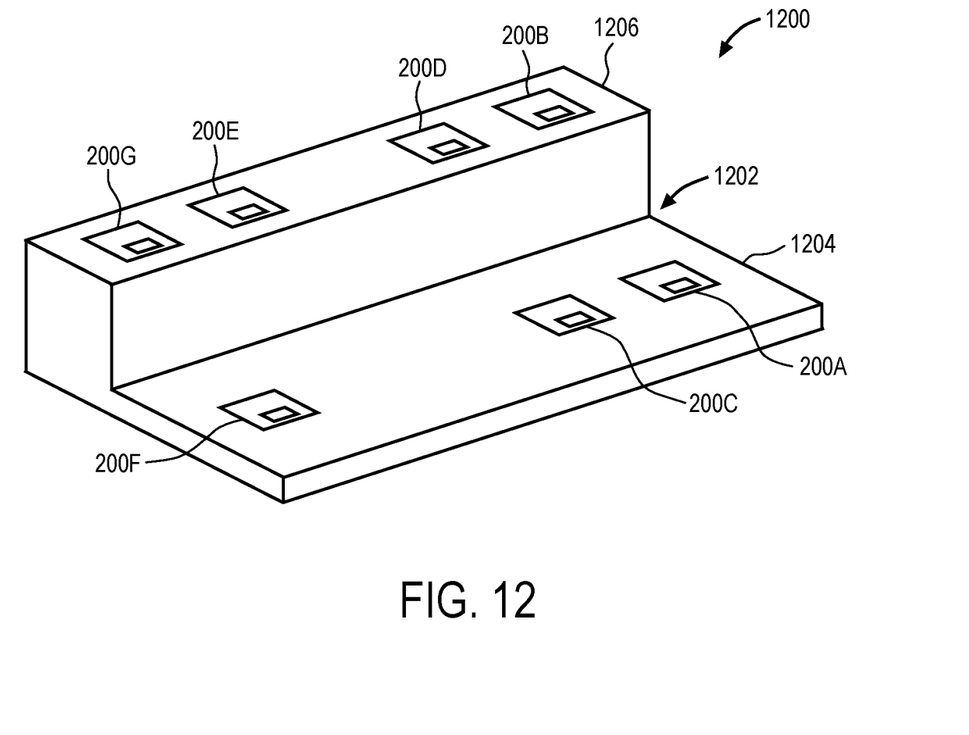
FIG. 12 is a top perspective view of one embodiment of a foot pedal assembly array.

It should further be understood that in some embodiments, one or more of the previously discussed foot pedal assemblies or foot pedals may be arranged in an array with respect to one another, and the position, motion and/or speed of the target object may be determined with respect to the assembles in the array. Representatively, FIG. 12 illustrates a perspective view of one embodiment of foot pedal assembly or system having an array of pedal assemblies. In particular, the assembly 1200 may include an array of pedal assemblies 200A, 200B, 200C, 200D, 200E, 200F and 200G. Although not specifically labeled in FIG. 12, each of pedal assemblies 200A-200G may be substantially the same as pedal assembly 200 and therefore include a foot pedal base, a foot pedal and one or more sensors built into the foot pedal, as previously discussed. It should further be understood that while each of assemblies 200A-200G are shown including a sensor, in some embodiments, only some of assemblies 200A-200G may include a sensor (e.g., only assemblies 200A-200D include a sensor). Each of pedal assemblies 200A-200G may be used to operate, actuate, activate, or otherwise control, a different function, robotic operation and/or device of the surgical system using the foot. For example, pedal assemblies 200A and 200C may be used to control devices such as surgical instruments (e.g., a scalpel), while pedal assemblies 200B and 200D may be used to control more specialized surgical devices such as surgical energy devices (e.g., a stapler, a laser or the like). In addition, pedal assemblies 200E-200G may control other more general functions and/or operations of the system. For example, pedal assembly 200F may control a camera, pedal assembly 200G may be a clutch and pedal assembly 200E may be used to change surgical devices.

Each of pedal assemblies 200A-200G may be arranged on, or otherwise mounted to, a foot pedal assembly platform 1202. Platform 1202 may include a lower portion 1204 and an upper portion 1206. The lower portion 1204 is considered to be "lower" because it is in a plane below the upper portion 1206. In some embodiments, the pedal assemblies controlling the more specialized devices such as energy devices (e.g., assemblies 200B and 200D) are arranged on the upper portion 1206 and those that control non-energy devices such as scalpels (e.g., assemblies 200A and 200C) are positioned on the lower portion 1204. In addition, the assemblies may be understood as being within a right hand side or a left hand side of the platform 1202, and may correspond to right or left hand operations of surgical tool 107, as previously discussed. For example, assemblies 200E-200G may be considered on the left hand side, while assemblies 200A-200D may be considered on the right hand side of platform 1202. In addition, within the assemblies on the right hand side, those on the left side (e.g., 200C-200D) may control left hand operations while those on the right side (e.g., 200A-200B) may control right hand operations.

Figure 13:
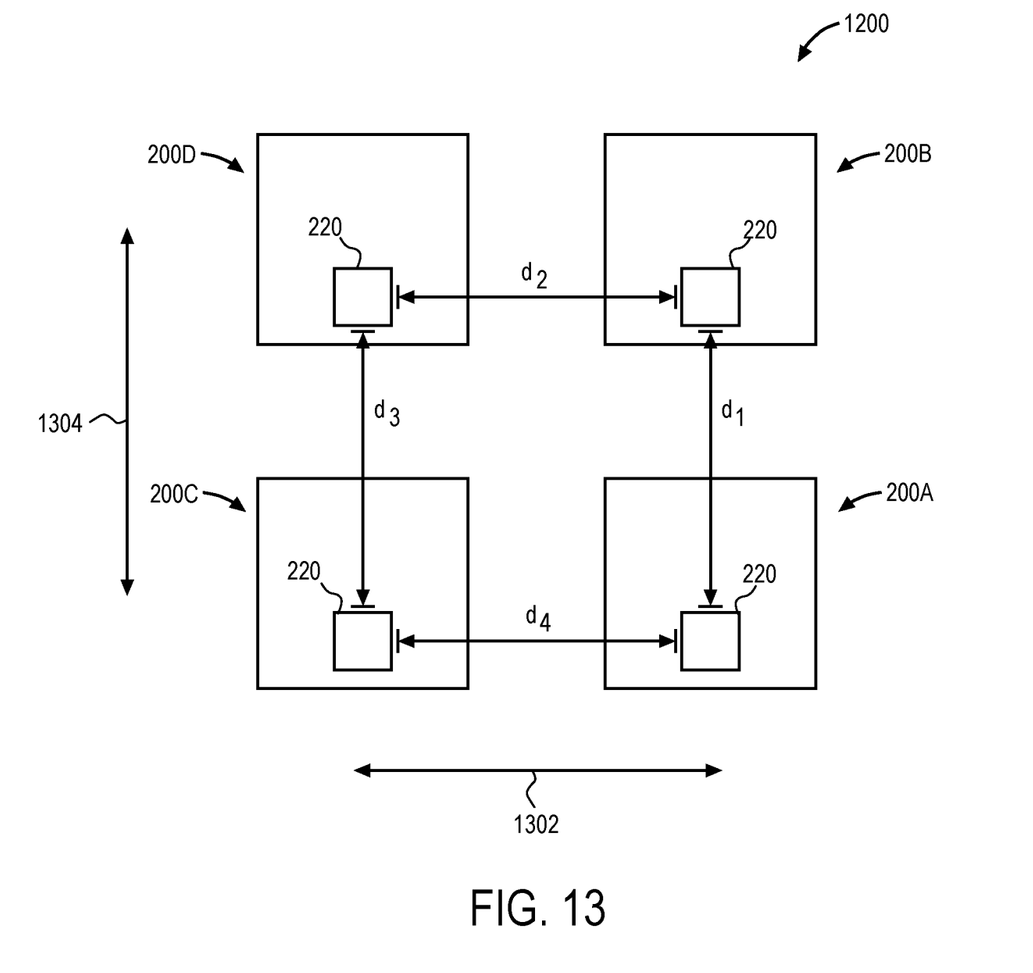
FIG. 13 is a schematic illustration of the foot pedal assembly array of FIG. 12.

In a similar manner to the previously discussed sensor arrays, the array of pedal assemblies 200A-200G may further be used to determine a position, motion and/or speed of a target object with respect to a particular pedal assembly 200A-200G. In addition, the detection of a target object with respect to one of the assemblies 200A-200G may be used to anticipate, or otherwise control, an activation of an adjacent pedal assembly or prevent activation of an adjacent pedal assembly. Representatively, as illustrated by the schematic diagram in FIG. 13, a distance ($d_1$, $d_2$, $d_3$, $d_4$) between each of the sensors 220 of the pedal assemblies 200A-200D is known, as are the locations of the sensors and associated pedals with respect to one another. Accordingly, the presence of a target object (e.g., a user's foot) by sensor 220 of one of the pedal assemblies 200A-200D (e.g., pedal assembly 200A), but not another, can be used to determine that the object is only over that particular pedal assembly (e.g., pedal assembly 200A). In addition, the sequential detection of the target object presence over one of the pedal assemblies 200A-200D, and then another of the pedal assemblies 200A-200D, can be used to determine that the object is moving from one pedal assembly to another. For example, the detection of the target object by pedal assembly 200A, followed by pedal assembly 200B, can be used to determine the object is moving in an axial (or front/back direction), as illustrated by arrow 1304. In addition, the detection of the target object by pedal assembly 200A, followed by pedal assembly 200D can be used to determine the object is moving in a lateral or left/right direction, as illustrated by arrow 1302. The speed of the object motion between the pedal assemblies 200A-200D can also be determined using similar information. This motion and speed knowledge can be particularly useful in providing the surgeon with critical information about results of any action they are about to take and assist in training users to optimize system use, as previously discussed.

Figure 14:
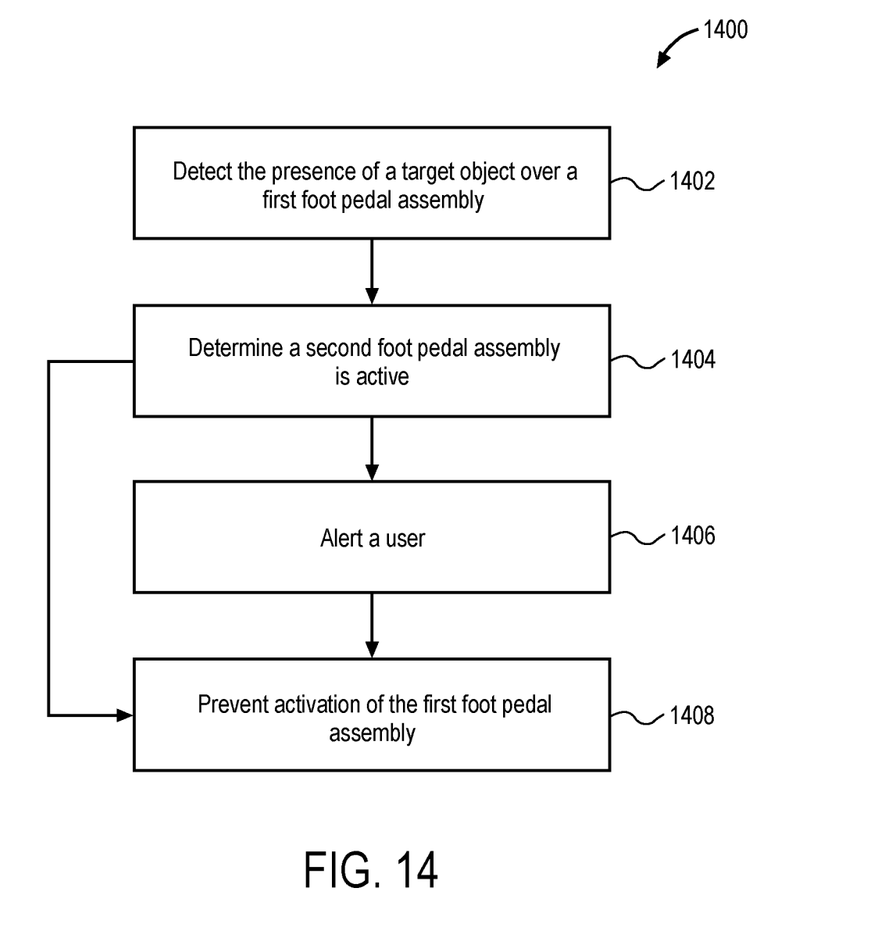
FIG. 14 is a flow chart of one embodiment of a process for alerting a user of the presence of a target object.

One exemplary process flow for determining the object motion is illustrated in FIG. 14. Representatively, process 1400 includes detecting the presence of the target object over one foot pedal assembly (block 1402), followed by detecting the target object over another foot pedal assembly (block 1404). The information detected with respect to each foot pedal assembly can then be used to alert a user that in addition to activating one pedal, their foot may be hovering over another pedal (block 1406). In addition, as previously discussed, some of the foot pedal assemblies activate energy or advanced functionality surgical devices and/or instruments. The unintentional activation of these devices may be very harmful. It is therefore critical that the user is aware of which pedal they are about to press before activation of the pedal, and that they not accidentally activate a pedal, particularly while another pedal is already activated. Therefore, in some embodiments, the process may further include preventing activation of a foot pedal assembly (block 1408). For example, information obtained by a sensor associated with one pedal assembly may be used to prevent activation of another pedal assembly, particularly while the one pedal assembly is active. Representatively, if pedal assembly 200A is currently active and controlling a robotic operation, and the presence of the target object is detected over pedal assembly 200B by the corresponding sensor 220, this suggests that the object is unintentionally being position over assembly 200B. For example, the user may be activating assembly 200A with their heal, and their toe may be accidentally positioned over a portion of assembly 200B. To prevent the unintentional activation of assembly 200B by the user, the system may alert the user of the presence of their toe over assembly 200B so that the user can adjust their foot position. For example, the alert may be a visual alert (e.g., on display 115), an audio alert (e.g., output by system 103), a tactile alert (e.g., at console 102), or any other type of alert sufficient to notify the detection of a potentially unintentional hover detection. In addition, in some embodiments, the system may automatically de-active or prevent activation of assembly 200B until assembly 200A is no longer active.

In addition, a pedal prioritization algorithm can be used to alert a user of an unintended operation or automatically prevent activation of one pedal with respect to another. For example, in some cases, when a user places their foot on an upper pedal (e.g., pedal assemblies 200B, 200D), the pedal sensor of a lower pedal assembly (e.g., pedal assemblies 200A, 200C) in addition to the upper pedal sensor will be triggered. A prioritization is therefore implemented so that if both the upper and lower pedal sensors detect an object on either the left or right side, the user is alerted of the upper pedal hover. In this case, the user may only be alerted to the upper pedal hover because the upper pedal controls energy functions, which if unintentionally activated, may result in more harm than the lower pedal function. In addition, in some embodiments, the system may automatically prevent or otherwise deactivate the lower pedal function under this scenario.

While certain embodiments have been described and shown in the accompanying drawings, it is to be understood that such embodiments are merely illustrative of and not restrictive on the broad invention, and that the invention is not limited to the specific constructions and arrangements shown and described, since various other modifications may occur to those of ordinary skill in the art. For example, while the Figures illustrate pedal assemblies for surgical operations, alternative applications may include any application in which it would be beneficial for a user of a system with multiple pedal-actuated functions to be alerted of which pedal their foot is on or over. Examples include medical devices, aviation, aerospace equipment, aviation equipment or the like. The description is thus to be regarded as illustrative instead of limiting.

What is claimed is:

1. A foot pedal assembly for controlling a robotic surgical system, the foot pedal assembly comprising:
   a foot pedal operable to activate a surgical tool of the robotic surgical system;
   a sensor operable to detect a target object hovering over the foot pedal; and
   a processor operable to provide an alert when the processor determines a close proximity between the target object and the foot pedal would result in an unintentional activation of the surgical tool and prevent the foot pedal from activating the surgical tool.

2. The foot pedal assembly of claim 1 wherein the close proximity corresponds to a distance detected by the sensor between the foot pedal and the target object that indicates an unintentional hovering of the target object over the foot pedal.

3. The foot pedal assembly of claim 1 wherein the processor determines contact would result in an unintentional activation of the surgical tool when another foot pedal is actively controlling another surgical tool.

4. The foot pedal assembly of claim 1 wherein the processor determines contact would result in an unintentional activation of the surgical tool when the surgical tool comprises an energy emitting tool.

5. The foot pedal assembly of claim 1 wherein the processor is further operable to prevent the foot pedal from activating the surgical tool when the processor determines contact between the target object and the foot pedal would result in the unintentional activation of the surgical tool.

6. The foot pedal assembly of claim 1 wherein the foot pedal is a first foot pedal and the sensor is a first sensor, and the assembly further comprises a second sensor operable to detect the target object hovering over the second foot pedal, and the processor determines contact would result in an unintentional activation of the surgical tool when hovering of the object is detected over both the first foot pedal and the second foot pedal.

7. The foot pedal assembly of claim 1 wherein the alert comprises an audio or a tactile alert.

8. The foot pedal assembly of claim 1 wherein the sensor is an optical sensor having an emitter and a detector, and the emitter emits a beam of electromagnetic radiation over the foot pedal.

9. The foot pedal assembly of claim 1 wherein the sensor is a capacitive sensor.

10. The foot pedal assembly of claim 1 wherein the sensor is one of an array of sensors coupled to a contact surface of the foot pedal.

11. The foot pedal assembly of claim 1 wherein the foot pedal assembly is one of an array of foot pedal assemblies operable to control different surgical robotic operations and the alert identifies which of the foot pedal assemblies the target object is hovering over.

12. The foot pedal assembly of claim 11 further comprising:
a foot pedal assembly platform having an upper platform and a lower platform to which the array of foot pedal assemblies are mounted.

13. A foot pedal system for controlling a robotic surgical system, the foot pedal system comprising:
a first foot pedal assembly and a second foot pedal assembly, each of the first foot pedal assembly and the second foot pedal assembly having a foot pedal and an optical sensor operable to detect a presence of a target object prior to activation of the first foot pedal assembly or the second foot pedal assembly by the target object; and
a processor operable to provide an alert when the processor determines activation of the first foot pedal assembly or the second foot pedal assembly by the target object would result in an unintentional surgical operation and prevent activation of the first foot pedal assembly or the second foot pedal assembly.

14. The foot pedal system of claim 13 wherein the processor determines activation would result in an unintentional surgical operation when at least one foot pedal is already actively controlling a surgical operation.

15. The foot pedal system of claim 13 wherein the processor further determines activation would result in an unintentional surgical operation when the surgical operation is an energy emitting operation.

16. The foot pedal system of claim 13 wherein the processor further determines activation would result in an unintentional surgical operation when hovering of the target object is detected over the foot pedal of the first foot pedal assembly and the second foot pedal assembly.

17. The foot pedal system of claim 16 wherein the processor is configured to prevent activation of the first foot pedal assembly when the presence of the target object is detected over the first foot pedal assembly while the second foot pedal assembly is actively controlling the surgical operation.

18. The foot pedal system of claim 13 wherein the optical sensor is one of an array of optical sensors coupled to different regions of a respective foot pedal, and the processor is further configured to determine a position of the target object corresponds to one of the different regions.

19. The foot pedal system of claim 13 wherein the processor is configured to determine the position of the target object with respect to the first foot pedal assembly based on the presence of the target object being detected by the optical sensor of the second foot pedal assembly.

20. The foot pedal system of claim 13 wherein the processor is further configured to determine a lateral motion of the target object when the presence of the target object is detected by the optical sensors in sequence.

* * * * *